United States Patent
Kakinuma et al.

(10) Patent No.: US 9,161,945 B2
(45) Date of Patent: Oct. 20, 2015

(54) 4-ISOPROPYL-6-METHOXYPHENYL GLUCITOL COMPOUND

(75) Inventors: Hiroyuki Kakinuma, Toshima-ku (JP); Yohei Kobashi, Toshima-ku (JP); Tomomichi Chonan, Toshima-ku (JP); Fumiyasu Shiozawa, Toshima-ku (JP); Yuki Iwata, Toshima-ku (JP); Takahiro Oi, Toshima-ku (JP); Kenichi Kawabe, Toshima-ku (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 356 days.

(21) Appl. No.: 13/817,666

(22) PCT Filed: Aug. 19, 2011

(86) PCT No.: PCT/JP2011/068738
§ 371 (c)(1),
(2), (4) Date: Feb. 19, 2013

(87) PCT Pub. No.: WO2012/023600
PCT Pub. Date: Feb. 23, 2012

(65) Prior Publication Data
US 2013/0165645 A1    Jun. 27, 2013

(30) Foreign Application Priority Data
Aug. 20, 2010 (JP) ................... 2010-184866

(51) Int. Cl.
| C08B 37/00 | (2006.01) |
| C07H 5/04 | (2006.01) |
| C07H 5/06 | (2006.01) |
| A61K 31/7034 | (2006.01) |
| A61K 31/351 | (2006.01) |
| C07D 309/10 | (2006.01) |

(52) U.S. Cl.
CPC ........... *A61K 31/7034* (2013.01); *A61K 31/351* (2013.01); *C07D 309/10* (2013.01)

(58) Field of Classification Search
CPC . C07D 309/10; A61K 31/351; A61K 31/7034
USPC ........................................................ 536/53
See application file for complete search history.

(56) References Cited

U.S. PATENT DOCUMENTS
2010/0022460 A1    1/2010  Kakinuma et al.
2011/0306759 A1   12/2011  Kakinuma et al.

FOREIGN PATENT DOCUMENTS
| JP | 2009107947 | 5/2009 |
| JP | 2009107948 | 5/2009 |
| JP | 2009537509 | 10/2009 |
| WO | 2007136116 | 11/2007 |
| WO | 2010095768 | 8/2010 |

OTHER PUBLICATIONS

Definition of prophylactic, Retrieved from www.medicinenet.com [online, retrieved on Jul. 28, 2008].*
Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
"Can Diabetes Be Prevented" from KidsHealth [online]. [Retrieved Apr. 20, 2015]. Retrieved from the internet <http://kidshealth.org/parent/medical/endocrine/prevention.html#> Reviewed Aug. 2013.*
Communication for EP Application No. 11818240.1 issued Dec. 5, 2013, with Supplementary European Search Report.
International Preliminary Report on Patentability for PCT/JP2011/068738 dated Mar. 19, 2013, with Written Opinion.

* cited by examiner

*Primary Examiner* — Scarlett Goon
(74) *Attorney, Agent, or Firm* — Sughrue Mion, PLLC

(57) ABSTRACT

A compound, which inhibits SGLT1 (sodium-dependent glucose transporter 1) activity to suppress absorption of glucose or the like, thereby suppressing abnormal glucose tolerance or postprandial hyperglycemia in diabetes, is provided. Specifically, a 4-isopropyl-6-methoxyphenyl glucitol compound represented by the following formula (I), or a pharmaceutically acceptable salt thereof, is provided:

[Chemical formula 1]

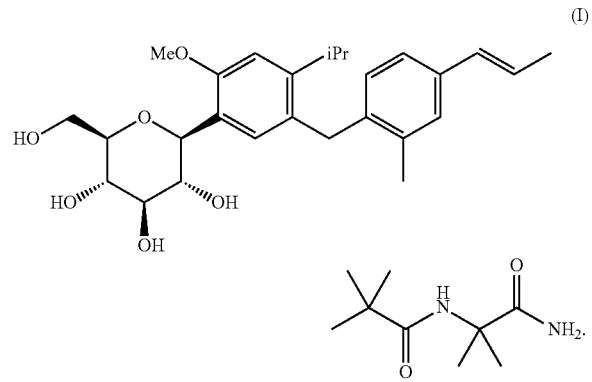

5 Claims, No Drawings

4-ISOPROPYL-6-METHOXYPHENYL GLUCITOL COMPOUND

TECHNICAL FIELD

This invention relates to a 4-isopropyl-6-methoxyphenyl glucitol compound which has inhibitory activity specific to sodium-dependent glucose transporter 1 (hereinafter abbreviated as "SGLT1" for convenience) involved in absorption of glucose and galactose in the small intestine.

BACKGROUND ART

Blood glucose levels are used as a biomarker for metabolic syndrome, and people are diagnosed as having diabetes if their fasting blood glucose levels exceed 126 mg/dL. Moreover, even if fasting blood glucose levels fall within a normal range, some people have 2-hour postprandial blood glucose levels as high as 140 to 200 mg/dL and are diagnosed as having impaired glucose tolerance (or postprandial hyperglycemia). Recent epidemiological studies have reported that impaired glucose tolerance increases the risk of cardiovascular disorders (see Non-Patent Documents 1 and 2). Further, it has been reported that exercise therapy and/or medication not only suppresses the development of type II diabetes from impaired glucose tolerance, but also significantly suppresses the onset of hypertension (see Non-Patent Document 3).

In view of the foregoing, suppression of postprandial hyperglycemia is of importance in suppressing the onset of diabetes and/or metabolic syndrome, and there has accordingly been an increasing demand for drugs used to control postprandial hyperglycemia.

As drugs for improving postprandial hyperglycemia, α-glucosidase inhibitors have been conventionally used widely, which inhibit sugar hydrolases and thereby delay sugar absorption from the small intestine. In addition to these agents, there have been developed other agents with a new mechanism of action for improving postprandial hyperglycemia.

On the mammalian small intestinal epithelium, sodium-dependent glucose transporter 1 (SGLT1) is expressed at a high frequency. It is known that SGLT1 serves depending upon sodium and plays a role in active transport of glucose or galactose in the small intestine. Based on these findings, pyrazole derivatives have been reported, which inhibit SGLT1 activity to thereby suppress glucose absorption from a meal and can be used for prevention or treatment of postprandial hyperglycemia (see Patent Documents 1 to 6). On the other hand, sodium-dependent glucose transporter 2 (SGLT2) is expressed at a high frequency in the kidney, and glucose once filtered by the glomeruli is reabsorbed via SGLT2 (see Non-Patent Document 4). Moreover, it has been reported that upon inhibition of SGLT2 activity, sugar excretion into urine is facilitated to induce a hypoglycemic action (see Non-Patent Document 5). SGLT2 inhibitors are characterized in that they have an excellent hypoglycemic action to lower casual blood glucose levels, but their action to control postprandial hyperglycemia is low, unlike SGLT1 inhibitors. Further, there is a report of C-phenyl glucitol derivatives which inhibit not only SGLT1 activity but also SGLT2 activity at the same time (see Patent Document 7).

On the other hand, in the case of drugs required to be administered continuously, including drugs for improving postprandial hyperglycemia, it is important to have a wide margin of safety between the therapeutic dose and the toxic or side effect dose. Particularly in the case of drugs prone to remain in the body, it is difficult to control their dosage required for treatment, so that an excessive drug effect will be developed as a result of summing residual drugs remaining in the body, thus leading to unexpected toxicity and side effects. For example, it is known that cationic drugs whose molecule has a hydrophilic group (e.g., a tertiary amine) and a hydrophobic group (e.g., an aromatic ring) bind to phospholipids through hydrophobic bonding and are taken up by lysosomes and hence accumulated in all organs in the body. As typical examples, chloroquine is shown to cause retinopathy, while perhexiline gives rise to a problem of neuropathy because it induces changes in the lung and cerebellum (see Non-Patent Document 6).

Thus, drugs are desired to be rapidly excreted from the body after developing their efficacy. In particular, drugs for improving postprandial hyperglycemia that must be administered continuously are desired to be free from the problem of accumulation in the body.

CITATION LIST

Patent Documents

Patent Document 1: International Publication WO2002/098893 pamphlet
Patent Document 2: International Publication WO2004/014932 pamphlet
Patent Document 3: International Publication WO2004/018491 pamphlet
Patent Document 4: International Publication WO2004/019958 pamphlet
Patent Document 5: International Publication WO2005/121161 pamphlet
Patent Document 6: International Publication WO2004/050122 pamphlet
Patent Document 7: International Publication WO2007/136116 pamphlet

Non-Patent Documents

Non-Patent Document 1: Pan X R, et al. Diabetes Care, Vol. 20, p. 537, 1997
Non-Patent Document 2: M Tominaga, et al. Diabetes Care, Vol. 22, p. 920, 1999
Non-Patent Document 3: J.-L. Chiasson, et al. Lancent, Vol. 359, p. 2072, 2002
Non-Patent Document 4: E. M. Wright, Am. J. Physiol. Renal. Physiol., Vol. 280, page F10, 2001
Non-Patent Document 5: G., Toggenburger, et al. Biochim. Biophys. Acta, Vol. 688, p. 557, 1982
Non-Patent Document 6: Folia Pharmacol. Jpn. Vol. 113, p. 19, 1999

SUMMARY OF INVENTION

Technical Problem

An object of the present invention is to provide a 4-isopropyl-6-methoxyphenyl glucitol compound or a salt thereof which exhibits SGLT1 inhibiting action with a wide margin of safety between a therapeutic dose and a toxic or side effect dose, as well as a pharmaceutical preparation comprising the same.

Solution to Problem

The C-phenyl glucitol derivatives described in Patent Document 7 were found to have a tendency to remain in the kidney without being excreted from within the body. Thus, the inventors of the present invention searched for a compound free from the problem of remaining in the body, and conducted diligent studies. As a result, they have found that the 4-isopropyl-6-methoxyphenyl glucitol compound of the formula (I) shown below, which is obtained, in particular, by introducing an isopropyl group and a methoxy group into the benzene ring directly bonded to the sugar moiety and introducing a butenoyl group having an amino group into another benzene ring, does not remain in the kidney, contrary to their expectations. This finding has led to the completion of the present invention.

Hereinbelow, aspects of the 4-isopropyl-6-methoxyphenyl glucitol compound of the present invention (hereinafter referred to as the "compound of the present invention") will be described.

(1) A 4-isopropyl-6-methoxyphenyl glucitol compound represented by the following formula (I), or a pharmaceutically acceptable salt thereof:

[Chemical formula 1]

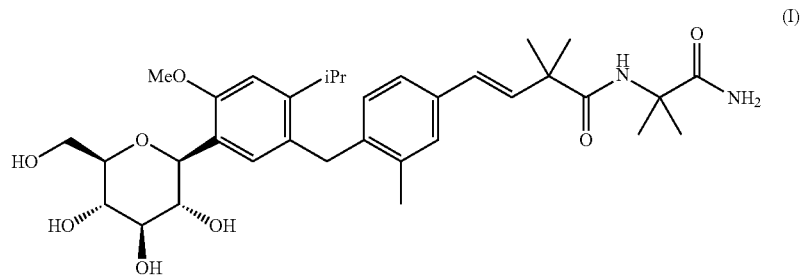

(I)

(2) A pharmaceutical composition which comprises the 4-isopropyl-6-methoxyphenyl glucitol compound according to (1) or the pharmaceutically acceptable salt thereof as an active ingredient.

(3) An inhibitor of sodium-dependent glucose transporter 1 (SGLT1) activity which comprises the 4-isopropyl-6-methoxyphenyl glucitol compound according to (1) or the pharmaceutically acceptable salt thereof as an active ingredient.

(4) A drug for improving postprandial hyperglycemia which comprises the 4-isopropyl-6-methoxyphenyl glucitol compound according to (1) or the pharmaceutically acceptable salt thereof as an active ingredient.

(5) A prophylactic or therapeutic preparation for diabetes which comprises the 4-isopropyl-6-methoxyphenyl glucitol compound according to (1) or the pharmaceutically acceptable salt thereof as an active ingredient.

(6) Use of the 4-isopropyl-6-methoxyphenyl glucitol compound according to (1) or the pharmaceutically acceptable salt thereof in the manufacture of a prophylactic or therapeutic preparation for diabetes.

Advantageous Effects of Invention

According to the present invention, it has become possible to provide a 4-isopropyl-6-methoxyphenyl glucitol compound which inhibits SGLT1 activity without remaining in the body.

DESCRIPTION OF EMBODIMENTS

The terms used in the present invention will be defined below.

The term "pharmaceutically acceptable salt" is intended to mean, for example, a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, a formate salt, an acetate salt, a propionate salt, a butyrate salt, a hexanoate salt, an octanoate salt, a trifluoroacetate salt, a maleate salt, a tartrate salt, a citrate salt, a stearate salt, a succinate salt, an ethylsuccinate salt, a lactobionate salt, a gluconate salt, a glucuronate salt, a glucoheptate salt, a glutarate salt, a pimelate salt, a suberate salt, an azelate salt, a sebacate salt, a 1,9-nonanedicarboxylate salt, a dodecanedioate salt, a tridecanedioate salt, a tetradecanedioate salt, a pentadecanedioate salt, a hexadecanedioate salt, a heptadecanedioate salt, a benzoate salt, a 2-hydroxybenzoate salt, a methanesulfonate salt, an ethanesulfonate salt, an ethanedisulfonate salt, a 2-hydroxyethanesulfonate salt, a benzenesulfonate salt, a p-toluenesulfonate salt, a 1,5-naphthalenedisulfonate salt, a lauryl sulfate salt, a lactate salt, a hippurate salt, a fumarate salt, a malonate salt, a trans-cinnamate salt, a malate salt, an aspartate salt, a glutamate salt, an adipate salt, a salt with cysteine, a salt with N-acetylcysteine, a hydrochloride salt, a hydrobromide salt, a phosphate salt, a sulfate salt, a hydroiodide salt, a nicotinate salt, an oxalate salt, a picrate salt, a thiocyanate salt, an undecanoate salt, a salt with an acrylate polymer, and a salt with a carboxyvinyl polymer.

The "compound of the present invention or the salt thereof" includes their pharmaceutically acceptable hydrates as well. The compound of the present invention or the salt thereof may be exposed to the atmosphere, or may absorb water during the production process to have adsorption water or may become a hydrate. Such a hydrate is included in the hydrates of the present invention.

The term "drug for improving postprandial hyperglycemia" is intended to mean a drug which suppresses postprandial hyperglycemia to thereby suppress the onset of postprandial hyperglycemia-related diseases (e.g., diabetes, metabolic syndrome) or treat such diseases. As used herein, the term "postprandial hyperglycemia" is intended to mean a state where blood glucose levels are abnormally elevated after a meal, more specifically a state where 2-hour postprandial blood glucose levels exceed 140 mg/dl.

The usefulness of the compound of the present invention will be described below (for details, see the test examples described later).

The compound of the present invention has strong SGLT1 inhibitory activity and also has some, although weak, SGLT2 inhibitory activity. Moreover, the compound of the present invention has a hypoglycemic effect as strong as that of the compounds disclosed in WO2007/136116. Furthermore, the compounds disclosed in WO2007/136116 tend to remain in the kidney without being excreted even at day 7 after oral administration at 1 mg/kg, whereas the compound of the present invention exhibited a characteristic feature in that even when it was administered for 3 consecutive days at a dose of 3 mg/kg, it unexpectedly did not remain in the kidney at subsequent day 2.

Thus, the compound of the present invention does not remain in the body and is less likely to cause side effects and toxicity due to continuous administration, and hence is believed to be excellent in practical applicability as a pharmaceutical preparation.

When the compound of the present invention is to be provided as a pharmaceutical preparation, various dosage forms such as solids and liquids may be adopted, as appropriate. In this case, a pharmaceutically acceptable carrier(s) may also be incorporated. Examples of such a carrier include commonly used excipients, extenders, binders, disintegrating agents, coating agents, sugar-coating agents, pH adjustors, solubilizers, or aqueous or non-aqueous solvents. The compound of the present invention and these carriers may be formulated into tablets, pills, capsules, granules, powders, dusts, liquids, emulsions, suspensions or other dosage forms.

For example, the compound of the present invention can be provided in the form of oral tablets by being mixed and tabletted with excipients and so on which are commonly used for manufacture of solid preparations.

Besides, the compound of the present invention is subjected to inclusion in α-, β- or γ-cyclodextrin or methylated cyclodextrin, whereby its solubility can be improved.

The dose of the compound of the present invention will vary depending on the disease, symptoms, body weight, age and sex of the patient, the route of administration, etc. However, the daily dose for adults is 0.1 to 1,000 mg/kg body weight, preferably 0.1 to 200 mg/kg body weight, and more preferably 0.1 to 10 mg/kg body weight. This dose can be administered once daily or in several divided portions per day.

Production Method 1

The compound (I) of the present invention can be synthesized in the following manner:

[Chemical Formula 2]

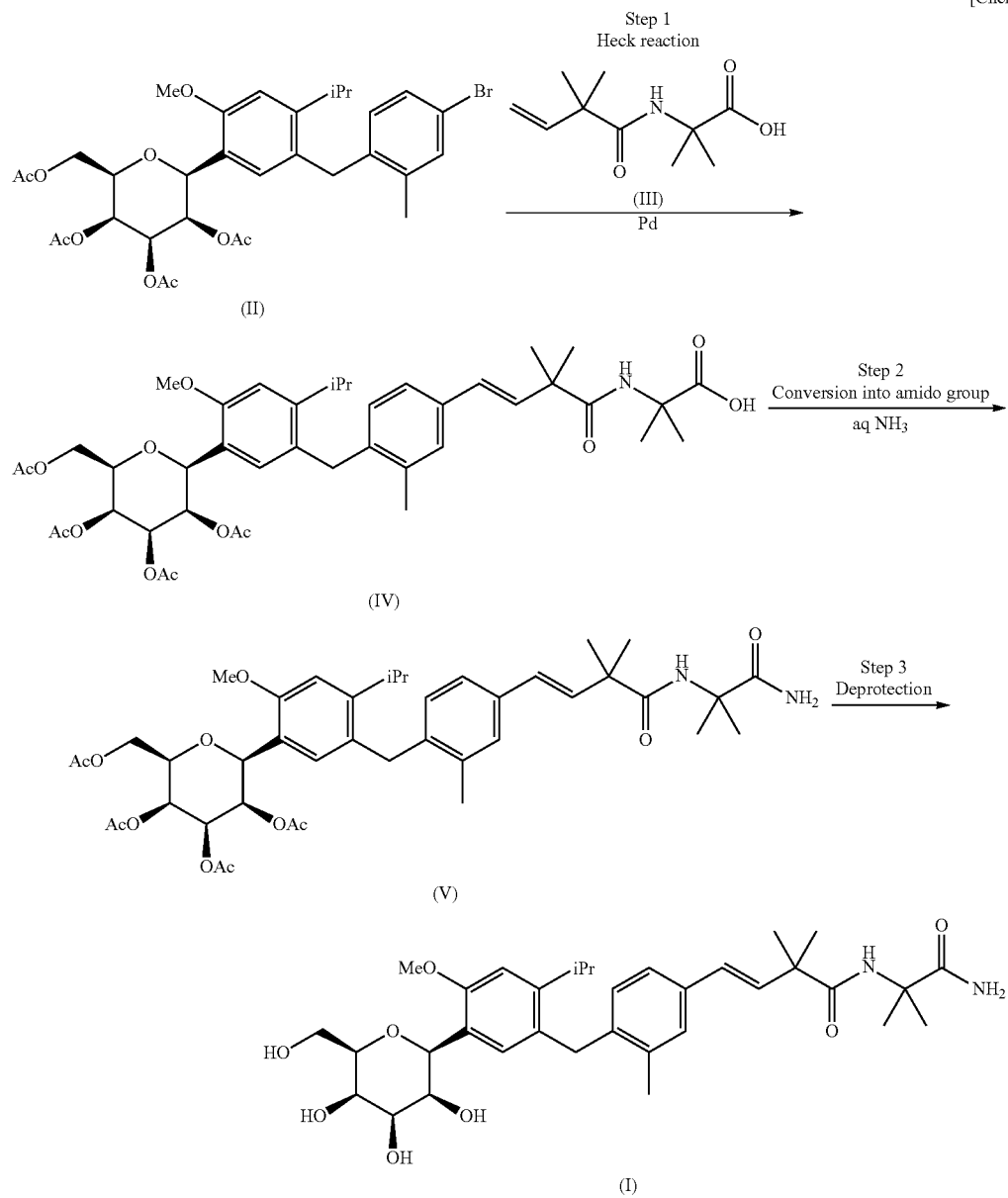

(1) Step 1 (Heck Reaction)

Compound (II) and olefinic carboxylic acid (III) may be subjected to Heck reaction in the presence of a palladium catalyst, a phosphine ligand and a suitable base to give compound (IV). Examples of the palladium catalyst used for this purpose include palladium acetate, tetrakis(triphenylphosphine)palladium, dibenzylideneacetonepalladium, bis(triphenylphosphine)palladium chloride, bis(tricyclohexylphosphine)palladium chloride, and palladium on activated carbon. Examples of the phosphine ligand include triphenylphosphine and tri-o-tolylphosphine. Likewise, examples of the base available for use include triethylamine, N,N-diisopropylethylamine, potassium carbonate, calcium carbonate, cesium carbonate, and potassium t-butoxide. Examples of a solvent used for the reaction include acetonitrile, toluene, and tetrahydrofuran. The reaction temperature is 0° C. to the reflux temperature, or a microwave may be used.

(2) Step 2 (Conversion into Amido Group)

Compound (IV) may be subjected to dehydration condensation with ammonia using a 28% aqueous solution of ammonia to give compound (V). Examples of a solvent used for this reaction include chloroform, dichloromethane, and N,N-dimethylformamide. Examples of the dehydration condensing agent include N,N'-dicyclohexylcarbodiimide (DCC), N-ethyl-N'-3-dimethylaminopropylcarbodiimide hydrochloride (EDC-HCl), 1,1'-carbonyldiimidazole (CDI), and EDC-HCl/1-hydroxybenzotriazole monohydrate (HOBt.H$_2$O). The reaction temperature in this case is 0° C. to 60° C.

(3) Step 3 (Deprotection)

The acetyl (Ac) groups of compound (V) may be removed under basic conditions to give compound (I). A base, such as sodium methoxide, sodium hydroxide, lithium hydroxide, potassium carbonate, cesium carbonate or triethylamine, can be used in the removal of the acetyl groups for deprotection. As a solvent, methanol, ethanol or aqueous methanol, for example, is named. The reaction temperature in this case is 0° C. to 60° C.

Production Method 2

The compound (I) of the present invention can also be synthesized by another route as shown below. The symbols shown there have the same meanings as those presented above.

[Chemical Formula 3]

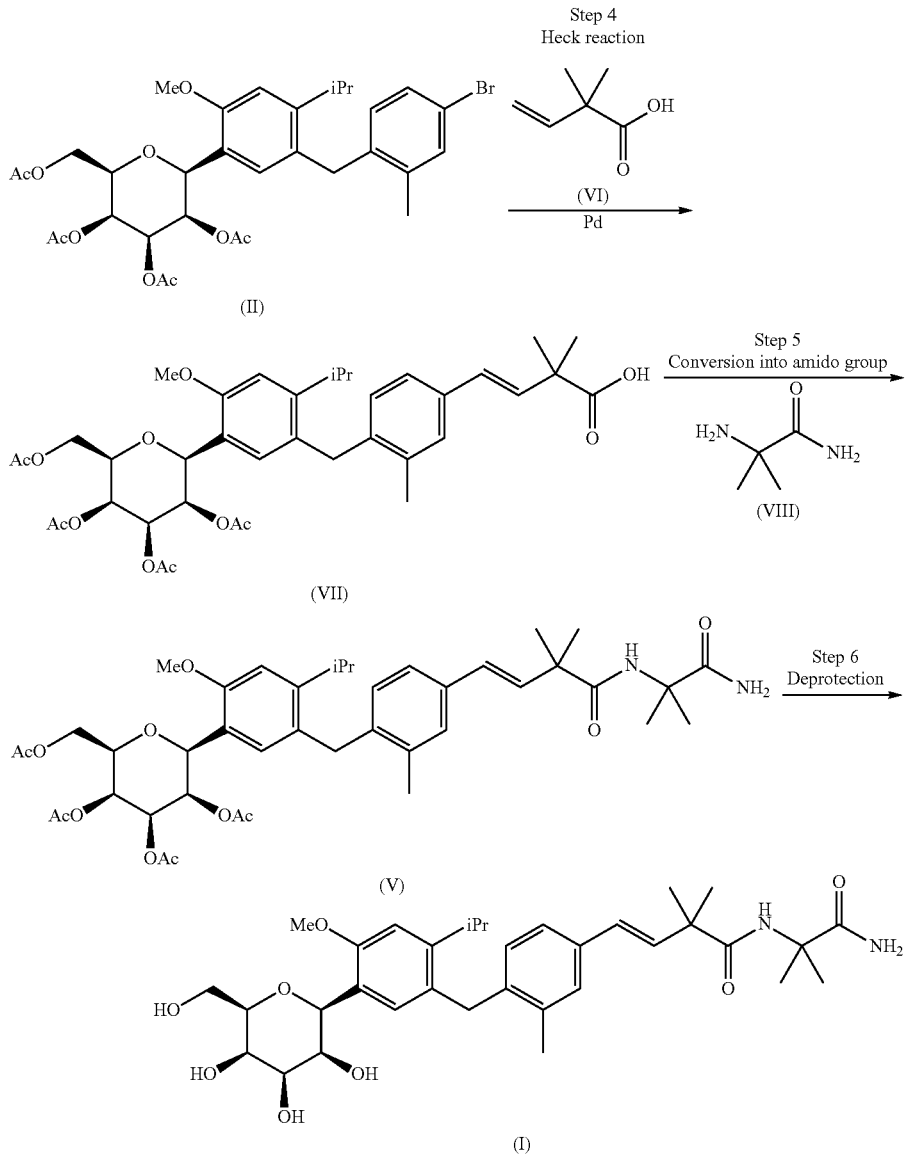

(4) Step 4 (Heck Reaction)

Compound (II) and olefin carboxylic acid (VI) may be used and subjected to Heck reaction as shown in Step 1 of Production method 1 to give compound (VII).

(5) Step 5 (Conversion into Amido Group)

Compound (VII) and amine (VIII) may be used and subjected to dehydration condensation as shown in Step 2 of Production method 1 to give compound (V).

(6) Step 6 (Deprotection)

Compound (V) obtained above may be converted into compound (I) by the deprotection reaction described in Step 3 of Production method 1.

Production Method 3

Method for Producing Intermediate (II)

A method for producing intermediate (II) necessary for the preparation of the compound (I) of the present invention will be shown below.

[Chemical Formula 4]

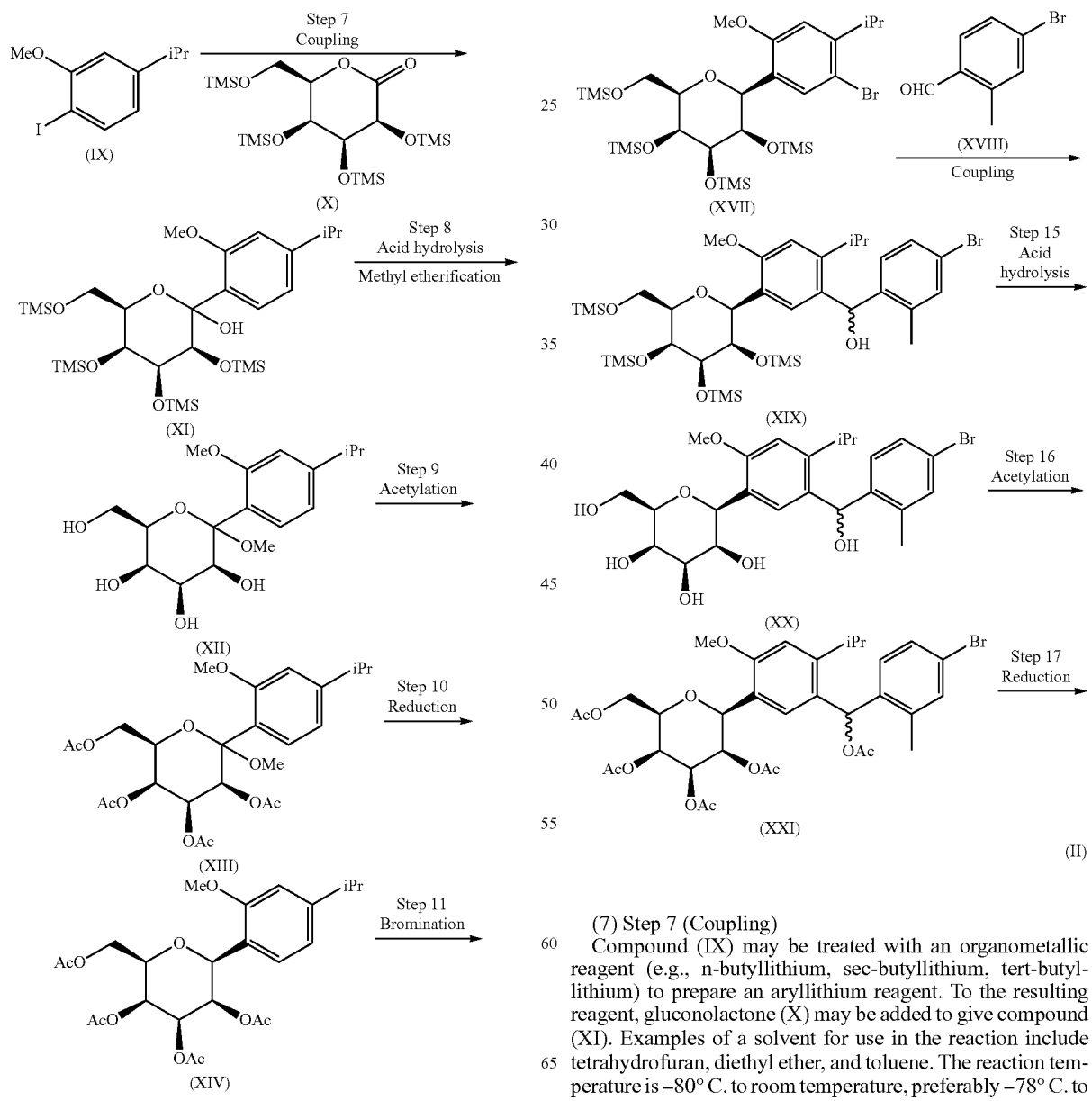

(7) Step 7 (Coupling)

Compound (IX) may be treated with an organometallic reagent (e.g., n-butyllithium, sec-butyllithium, tert-butyllithium) to prepare an aryllithium reagent. To the resulting reagent, gluconolactone (X) may be added to give compound (XI). Examples of a solvent for use in the reaction include tetrahydrofuran, diethyl ether, and toluene. The reaction temperature is −80° C. to room temperature, preferably −78° C. to −25° C.

(8) Step 8 (Acid Hydrolysis and Methyl Etherification)

Along with removing the silyl groups in compound (XI) in methanol under acidic conditions, the 1-position of the sugar moiety may be methyl-etherified to give compound (XII). Examples of an acid used for this purpose include hydrochloric acid, sulfuric acid, methanesulfonic acid, p-toluenesulfonic acid monohydrate, and pyridinium p-toluenesulfonate. Although the reaction temperature will vary depending on the acid to be used, it is 0° C. to 100° C., preferably 25° C. to 80° C.

(9) Step 9 (Acetylation)

The hydroxyl groups in compound (XII) may be protected with acetyl groups give compound (XIII). Compound (XII) may be reacted with, for example, acetic anhydride or acetyl chloride in a solvent in the presence of a suitable base to give compound (XIII). Examples of the solvent for use in the reaction include chloroform, dichloromethane, dioxane, ethyl acetate, tetrahydrofuran, and N,N-dimethylformamide. As the base, triethylamine, collidine, pyridine or the like may be used. As a catalyst for the reaction, 4-dimethylaminopyridine may also be used. The reaction temperature in this case is 0° C. to room temperature.

(10) Step 10 (Reduction)

Compound (XIII) may be reacted with $Et_3SiH$, $i\text{-}Pr_3SiH$, $t\text{-}BuMe_2SiH$ or $Ph_2SiHCl$ are reacted in the presence of an acid to give compound (XIV). Examples of the acid used in this reaction include $BF_3.OEt_2$, $CF_3COOH$, $InCl_3$, $TiCl_4$, TMSOTf, p-toluenesulfonic acid, and methanesulfonic acid. As a solvent, chloroform, dichloromethane, toluene, tetrahydrofuran, acetonitrile, or a solvent mixture of them is named, and preferred is a solvent mixture of acetonitrile and other solvent(s), such as acetonitrile/chloroform, acetonitrile/dichloromethane, acetonitrile/tetrahydrofuran, or acetonitrile/tetrahydrofuran/toluene. The reaction temperature in this case is −60° C. to 25° C., preferably −30° C. to 25° C.

(11) Step 11 (Bromination)

Compound (XIV) may be reacted with bromine, N-bromosuccinimide, hydrogen bromide or the like in a solution to give compound (XV). Examples of a solvent for use in the reaction include chloroform, dichloromethane, acetic acid, methanol, and N,N-dimethylformamide. The reaction temperature in this case is 0° C. to room temperature.

(12) Step 12 (Deprotection)

The acetyl groups in compound (XV) may be removed under basic conditions to give compound (XVI). As the base, sodium methoxide, sodium hydroxide, lithium hydroxide, potassium carbonate, cesium carbonate, triethylamine or the like can be used. As a solvent, methanol, ethanol, aqueous methanol or the like can be used. The reaction temperature in this case is 0° C. to 60° C.

(13) Step 13 (Silylation)

The hydroxyl groups in compound (XVI) may be protected with silyl groups such as trimethylsilyl groups to give compound (XVII). Compound (XVI) may be reacted with trimethylsilyl chloride, triethylsilyl chloride, tert-butyldimethylsilyl chloride or the like in a solvent in the presence of a suitable base to give compound (XVII). Examples of the solvent for use in the reaction include chloroform, dichloromethane, dioxane, ethyl acetate, tetrahydrofuran, and N,N-dimethylformamide. As the base, triethylamine, collidine, pyridine or the like can be used. The reaction temperature in this case is 0° C. to room temperature.

(14) Step 14 (Coupling)

Compound (XVII) may be treated with an organometallic reagent (e.g., n-butyllithium, sec-butyllithium, tert-butyllithium) to prepare an aryllithium reagent. To the resulting reagent, aldehyde (XVIII) may be added to give compound (XIX). Examples of a solvent for use in the reaction include tetrahydrofuran, diethyl ether, and toluene. The reaction temperature is −80° C. to room temperature, preferably −78° C. to −25° C.

(15) Step 15 (Acid Hydrolysis)

Compound (XIX) obtained above may be converted into compound (XX) by the same method as for the acid hydrolysis reaction described in Step 8 of Production method 3.

(16) Step 16 (Acetylation)

Compound (XX) obtained above may be converted into compound (XXI) by the acetylation reaction described in Step 9 of Production method 3.

(17) Step 17 (Reduction)

Compound (XXI) obtained above may be converted into intermediate (II) by the reduction reaction described in Step 10 of Production method 3.

Production Method 4

Method for Producing Intermediate (II)

Intermediate (II) can also be synthesized by another route as shown below. In this route, Steps 18 to 20 may be performed in one pot to thereby reduce the number of steps.

The symbols shown there have the same meanings as those presented above.

[Chemical Formula 5]

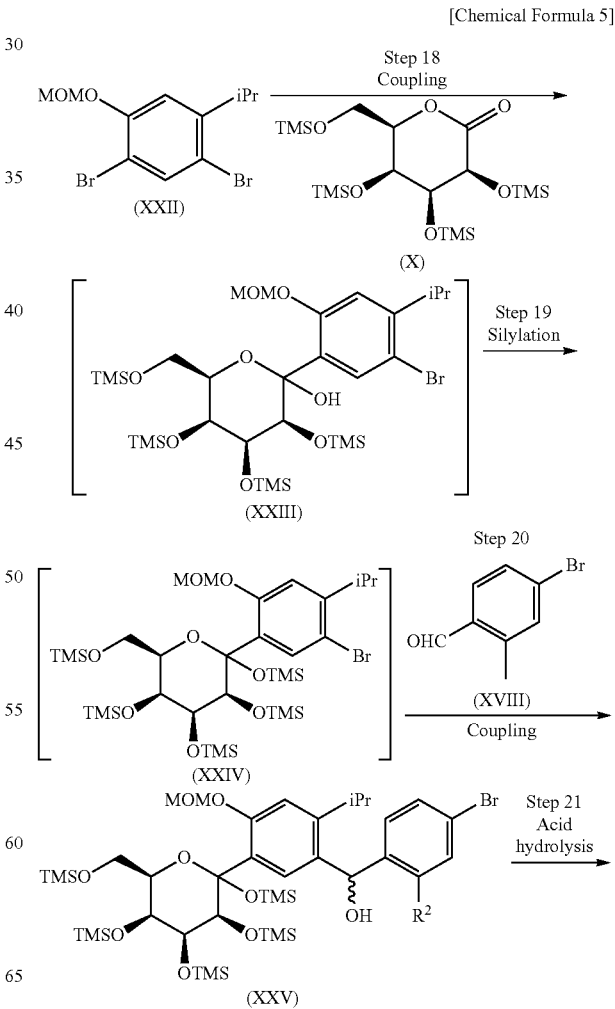

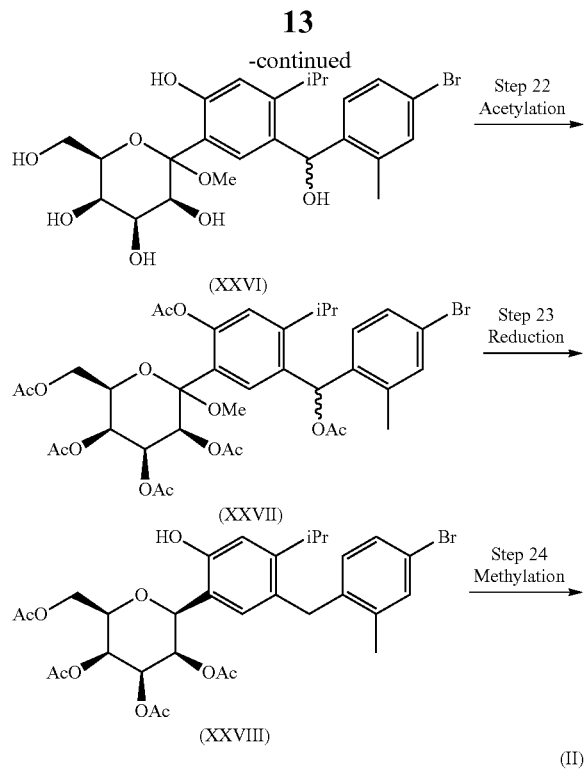

(XXVI)

Step 22
Acetylation (XXVII)

Step 23
Reduction (XXVIII)

Step 24
Methylation (II)

(18) Step 18 (Coupling)

Compound (XXII) may be treated with an organometallic reagent (e.g., n-butyllithium, sec-butyllithium, tert-butyllithium) to prepare an aryllithium reagent. To the resulting reagent, gluconolactone (X) may be added to give compound (XXIII). Examples of a solvent for use in the reaction include tetrahydrofuran, diethyl ether, and toluene. The reaction temperature is −80° C. to room temperature, preferably −78° C. to −25° C.

(19) Step 19 (Silylation)

Subsequently to Step 18 above, the hydroxyl group at the 1-position of compound (XXIII) may be protected with a silyl group such as a trimethylsilyl group. Trimethylsilyl chloride is reacted with the reaction mixture of Step 18 to give compound (XXIV). A solvent used in the reaction and the reaction temperature are the same as those in Step 18.

(20) Step 20 (Coupling)

Subsequently to Step 19 above, compound (XXIV) thus generated may be treated with an organometallic reagent (e.g., n-butyllithium, sec-butyllithium, tert-butyllithium) to prepare an aryllithium reagent. To the resulting reagent, aldehyde (XVIII) may be added to give compound (XXV). A solvent used in the reaction and the reaction temperature are the same as those in Step 18.

(21) Step 21 (Acid Hydrolysis)

Compound (XXV) obtained above may be converted into compound (XXVI) by the acid hydrolysis reaction described in Step 8 of Production method 3.

(22) Step 22 (Acetylation)

Compound (XXVI) obtained above may be converted into compound (XXVII) by the acetylation reaction described in Step 9 of Production method 3.

(23) Step 23 (Reduction)

Compound (XXVII) obtained above may be converted into compound (XXVIII) by the reduction reaction described in Step 10 of Production method 3.

(24) Step 24 (Alkylation)

The hydroxyl group in compound (XXVIII) may be methylated to prepare intermediate (II). Compound (XXVIII) may be reacted with methyl iodide in a solvent in the presence of a suitable base to give intermediate (II). Examples of the solvent for use in the reaction include chloroform, dichloromethane, tetrahydrofuran, N,N-dimethylformamide, and acetone. As the base, potassium carbonate, cesium carbonate or the like can be used.

REFERENCE EXAMPLE 1

Production of Intermediate (A)

[Chemical Formula 6]

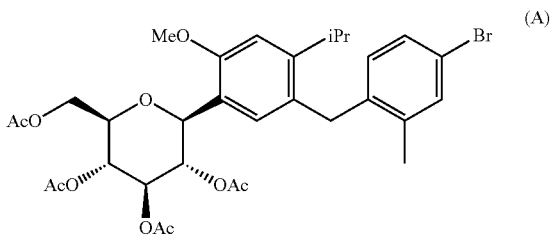

(A)

(1) Step 1 Compound (A1)

[Chemical Formula 7]

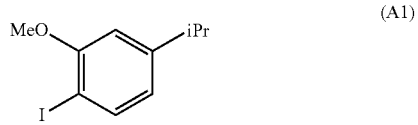

(A1)

To a solution of 3-isopropylphenol (25.0 g, 0.184 mol) in acetic acid (200 mL), a suspension of potassium iodate (7.88 g, 0.0368 mol) in water (75 mL) and iodine (18.7 g, 0.0736 mol) were added. This reaction mixture was stirred at room temperature for 20 hours. After addition of diethyl ether (400 mL) and water (300 mL), the organic layer was separated. The organic layer was washed with water, a saturated aqueous solution of sodium hydrogen carbonate and brine, and then dried over anhydrous magnesium sulfate. After filtering off the desiccant, the solvent was distilled off under reduced pressure. The resulting residue was purified by silica gel column chromatography (hexane:ethyl acetate=95:5) to give 2-iodo-5-isopropylphenol (27.6 g, 57%) as a colorless oil.

$^1$H NMR (200 MHz, CHLOROFORM-d) δ ppm 1.16-1.25 (m, 6 H) 2.64-2.98 (m, 1 H) 5.21 (s, 1 H) 6.57 (dd, J=8.13, 2.20 Hz, 1 H) 6.88 (d, J=2.20 Hz, 1 H) 7.54 (d, J=8.13 Hz, 1H).

Methyl iodide (9.8 mL, 0.156 mol) was added to an acetonitrile suspension (200 mL) of 2-iodo-5-isopropylphenol (27.4 g, 0.104 mol) and potassium carbonate (21.7 g, 0.156 mol), and the mixture was stirred at 40° C. for 2.5 hours. Methyl iodide (3.5 mL, 0.052 mol) was further added, and the mixture was stirred at the same temperature for 1 hour. Insolubles were filtered off, and the filtrate was diluted with ethyl acetate. The organic layer was washed with water, a 10% aqueous solution of sodium thiosulfate and brine, and dried over anhydrous magnesium sulfate. After filtering off the desiccant, the solvent was distilled off under reduced pressure. The resulting residue was purified by silica gel column chromatography (hexane→hexane:ethyl acetate=95:5) to give light yellow oily compound (A1) (24.5 g, 85%).

$^1$H NMR (300 MHz, CHLOROFORM-d) δ ppm 1.24 (d, J=6.84 Hz, 6 H) 2.87 (sept, J=6.84 Hz, 1 H) 3.88 (s, 3 H) 6.58-6.65 (m, 1 H) 6.70 (d, J=1.87 Hz, 1 H) 7.65 (d, J=8.08 Hz, 1 H).

MS ESI/APCI Dual posi: 277[M+H]$^+$.

(2) Step 2 Compound (A2)

[Chemical Formula 8]

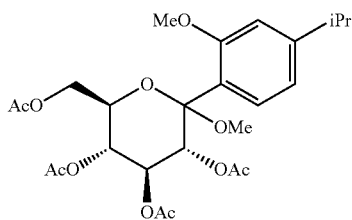

(A2)

To a solution of compound (A1) (24.5 g, 88.6 mmol) in THF (100 mL), a solution of 2.6M n-butyllithium in hexane (34 mL, 88.6 mmol) was added dropwise at −78° C. under a nitrogen atmosphere, and the mixture was stirred at the same temperature for 5 minutes. Then, a solution of 2,3,4,6-tetra-O-trimethylsilyl-D-glucono-1,5-lactone (37.6 g, 80.5 mmol) in THF (60 mL) was added dropwise over 25 minutes, and the mixture was stirred at the same temperature for 10 minutes. Ice and water were added to the reaction mixture, and the resulting mixture was warmed to room temperature and then extracted with ethyl acetate. The organic layer combined was washed with brine, and dried over anhydrous magnesium sulfate. After filtering off the desiccant, the solvent was distilled off under reduced pressure.

The resulting residue was dissolved in a solution containing methanesulfonic acid (1.55 g, 16.1 mmol) in methanol (380 mL), and the solution was stirred at room temperature for 2 hours. Then, the solution was neutralized with triethylamine (11.2 mL, 80.5 mmol), and the reaction mixture was concentrated.

The resulting residue (30.2 g) was dissolved in pyridine (100 mL), and acetic anhydride (100 mL) was added, followed by stirring the mixture for 14 hours at room temperature. Iced water (400 mL) was added, and the mixture was extracted twice with ethyl acetate (200 mL). The organic layer combined was washed with 1M hydrochloric acid, a saturated aqueous solution of sodium hydrogen carbonate and brine, and dried over anhydrous magnesium sulfate. After filtering off the desiccant, the solvent was distilled off under reduced pressure. The resulting residue was purified by silica gel column chromatography (hexane→hexane:ethyl acetate=6:4) to give light yellow oily compound (A2) (32.8 g, 80%; 3 steps).

$^1$H NMR (300 MHz, CHLOROFORM-d) δ ppm 1.23 (d, J=6.92 Hz, 6 H) 1.84 (s, 3 H) 1.97 (s, 3 H) 2.06 (s, 3 H) 2.10 (s, 3 H) 2.87 (sept, J=6.92 Hz, 1 H) 3.32 (s, 3 H) 3.87 (s, 3 H) 4.04 (ddd, J=10.18, 4.74, 2.41 Hz, 1 H) 4.17-4.23 (m, 1 H) 4.28-4.36 (m, 1 H) 5.25 (dd, J=10.18, 9.40 Hz, 1 H) 5.36 (d, J=10.18 Hz, 1 H) 5.60 (dd, J=10.18, 9.40 Hz, 1 H) 6.74 (d, J=1.55 Hz, 1 H) 6.79 (dd, J=8.08, 1.55 Hz, 1 H) 7.26-7.33 (m, 1 H).

MS ESI/APCI Dual posi: 533[M+Na]$^+$.

(3) Step 3 Compound (A3)

[Chemical Formula 9]

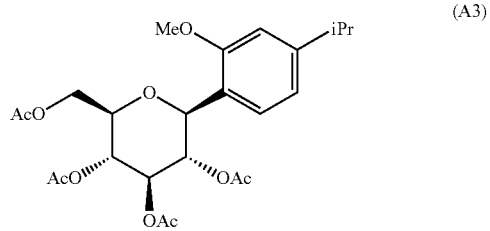

(A3)

To a solution of compound (A2) (32.8 g, 64.0 mmol) in chloroform (150 mL) and acetonitrile (150 mL), Et$_3$SiH (21 mL, 128 mmol) and BF$_3$.OEt$_2$ (49 mL, 385 mmol) were added at 4° C. under a nitrogen atmosphere, and the mixture was stirred at the same temperature for 1 hour. A saturated aqueous solution of sodium hydrogen carbonate was added to the reaction mixture, and the resulting mixture was extracted with chloroform. Then, the organic layer was washed with brine, and dried over anhydrous magnesium sulfate. After filtering off the desiccant, the solvent was distilled off under reduced pressure. The resulting residue was purified by silica gel column chromatography (hexane:ethyl acetate=2:1) to give a light yellow gummy compound (A3) (22.9 g, 74%).

$^1$H NMR (300 MHz, CHLOROFORM-d) δ ppm 1.22 (d, J=6.96 Hz, 6 H) 1.77 (s, 3 H) 2.01 (s, 3 H) 2.05 (s, 3 H) 2.07 (s, 3 H) 2.87 (sept, J=6.96 Hz, 1 H) 3.80-3.87 (m, 1 H) 3.84 (s, 3H) 4.09-4.16 (m, 1 H) 4.22-4.29 (m, 1 H) 4.88-4.95 (m, 1 H) 5.18-5.27 (m, 1 H) 5.32-5.38 (m, 2 H) 6.71 (d, J=1.55 Hz, 1 H) 6.83 (dd, J=7.93, 1.55 Hz, 1 H) 7.23-7.30 (m, 1 H).

MS ESI/APCI Dual posi: 503[M+Na]$^+$.
MS ESI/APCI Dual nega: 515[M+Cl]$^-$.

(4) Step 4 Compound (A4)

[Chemical Formula 10]

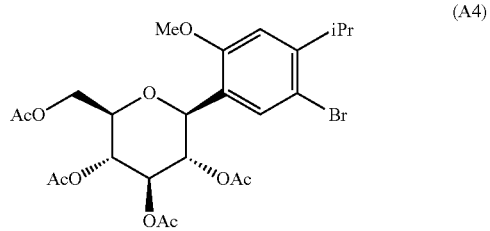

(A4)

To a solution of compound (A3) (22.9 g, 47 6 mmol) in acetic acid (90 mL), bromine (2.4 mL, 47.6 mmol) was added dropwise at room temperature. The reaction mixture was stirred for 1 hour, and poured into a saturated aqueous solution of sodium hydrogen carbonate (400 mL). The mixture was extracted twice with ethyl acetate, and the organic layer combined was washed with a 10% aqueous solution of sodium chloride, and dried over anhydrous magnesium sulfate. After filtering off the desiccant, the solvent was distilled off under reduced pressure. The resulting residue was purified by silica gel column chromatography (hexane:ethyl acetate=3:2) to give compound (A4) (25.5 g, 96%).

$^1$H NMR (300 MHz, CHLOROFORM-d) δ ppm 1.20 (d, J=6.84 Hz, 3 H) 1.23 (d, J=6.84 Hz, 3 H) 1.80 (s, 3 H) 2.01 (s, 3 H) 2.05 (s, 3 H) 2.09 (s, 3 H) 3.31 (sept, J=6.84 Hz, 1 H) 3.77-3.82 (m, 1 H) 3.83 (s, 3 H) 4.10-4.17 (m, 1 H) 4.22-4.30 (m, 1 H) 4.83 (d, J=9.48 Hz, 1 H) 5.17-5.38 (m, 3 H) 6.75 (s, 1 H) 7.49 (s, 1 H).

MS ESI/APCI Dual posi: 581[M+Na]⁺, 583[M+2+Na]⁺.

(5) Step 5 Compound (A5)

[Chemical Formula 11]

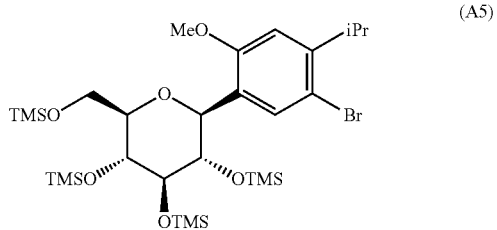

To a solution of compound (A4) (25.5 g, 45 6 mmol) in methanol (100 mL), sodium methoxide (4.88M/MeOH, 0.47 mL) was added. The reaction mixture was stirred at room temperature for 2 hours, and dry ice was added for neutralization. Then, the solvent was distilled off under reduced pressure.

The resulting residue was dissolved in N,N-dimethylformamide (135 mL), and triethylamine (45 mL, 319 mmol) and chlorotrimethylsilane (35 mL, 274 mmol) were added at 4° C. under a nitrogen atmosphere. The reaction mixture was stirred at room temperature for 2 hours, and iced water (300 mL) was added. This mixture was extracted three times with toluene, and the organic layer combined was washed with brine, and dried over anhydrous magnesium sulfate. After filtering off the desiccant, the solvent was distilled off under reduced pressure to give oily compound (A5) (32.2 g). This compound was used for the next reaction without being purified.

¹H NMR (300 MHz, CHLOROFORM-d) δ ppm −0.32 (s, 9 H) 0.09 (s, 9 H) 0.18 (s, 9 H) 0.20 (s, 9 H) 1.19 (d, J=6.84 Hz, 3 H) 1.23 (d, J=6.84 Hz, 3 H) 3.26-3.44 (m, 3 H) 3.52-3.58 (m, 2 H) 3.65-3.75 (m, 1 H) 3.76-3.83 (m, 1 H) 3.80 (s, 3 H) 4.60 (d, J=8.55 Hz, 1 H) 6.72 (s, 1 H) 7.51 (s, 1 H).

MS ESI/APCI Dual posi: 701[M+Na]⁺, 703[M+2+Na]⁺.

(6) Step 6 Compound (A6)

[Chemical Formula 12]

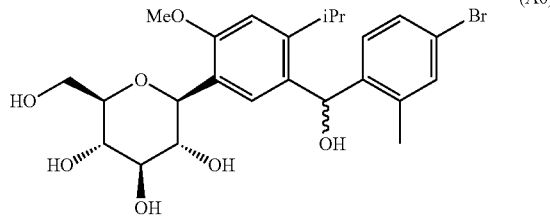

To a solution of compound (A5) (30.3 g, 44.5 mmol) in THF (200 mL), a solution of 2.6M n-butyllithium in hexane (16.9 mL, 44.5 mmol) was added dropwise over 3 minutes at −78° C. under a nitrogen atmosphere, and the mixture was stirred at the same temperature for 10 minutes. Then, a solution of 4-bromo-2-methylbenzaldehyde (9.7 g, 49.0 mmol) in THF was added dropwise over 15 minutes, and the mixture was stirred at the same temperature for 15 minutes. Water (100 mL) was added to the reaction mixture. This mixture was warmed to room temperature and then extracted twice with ethyl acetate. The organic layer combined was washed with brine, and dried over anhydrous magnesium sulfate. After filtering off the desiccant, the solvent was distilled off under reduced pressure.

The resulting residue was dissolved in a solution containing methanesulfonic acid (0.855 g) in methanol (200 mL), and the solution was stirred at room temperature for 0.5 hour. After neutralization with triethylamine, the reaction mixture was concentrated. The resulting residue was purified by silica gel column chromatography (chloroform:methanol=10:1→8:1) to give colorless amorphous compound (A6) (14.7 g, 60%).

¹H NMR (300 MHz, CHLOROFORM-d) δ ppm 1.23 and 1.25 (each d, J=6.84 Hz, 6 H) 1.80 (s, 2 H) 2.27 and 2.29 (each s, 3 H) 2.30-2.58 (m, 2 H) 2.82-3.06 (m, 2 H) 3.34 and 3.35 (each s, 3 H) 3.38-3.86 (m, 6 H) 4.56-4.73 (m, 1 H) 5.53 (d, J=3.11 Hz, 1 H) 6.75-7.35 (m, 5 H).

MS ESI/APCI Dual posi: 493[M−OH]⁺, 495[M+2−OH]⁺

(7) Step 7 Intermediate (A)

[Chemical Formula 13]

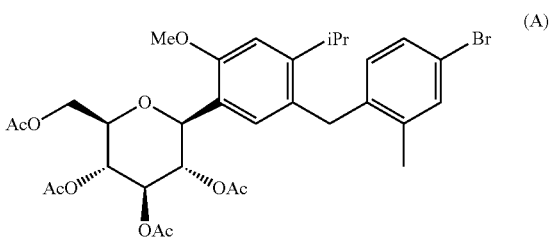

Compound (A6) (14.7 g, 28.7 mmol) was dissolved in pyridine (90 mL). Acetic anhydride (45 mL) was added to the resulting solution, and the mixture was stirred at room temperature for 15 hours. After addition of iced water (500 mL), the mixture was extracted twice with ethyl acetate (500 mL). The organic layer combined was washed with 2M hydrochloric acid and brine, and dried over anhydrous magnesium sulfate. After filtering off the desiccant, the solvent was distilled off under reduced pressure to give a crude product.

To a solution of this crude product (17.5 g) in chloroform (125 mL) and acetonitrile (125 mL), Et₃SiH (5.8 mL, 36.5 mmol) and BF₃·OEt₂ (4.6 mL, 36.5 mmol) were added at 4° C. under a nitrogen atmosphere. The reaction mixture was stirred for 0.5 hour. A saturated aqueous solution of sodium hydrogen carbonate was added to the reaction mixture, and the resulting mixture was extracted with chloroform. Then, the organic layer was washed with brine, and dried over anhydrous magnesium sulfate. After filtering off the desiccant, the solvent was distilled off under reduced pressure. The resulting residue was purified by silica gel column chromatography (hexane:ethyl acetate=2:1) to give colorless amorphous intermediate (A) (14.2 g, 88%).

¹H NMR (300 MHz, CHLOROFORM-d) δ ppm 1.11 (d, J=6.68 Hz, 3 H) 1.14 (d, J=6.68 Hz, 3 H) 1.75 (s, 3 H) 1.99 (s, 3 H) 2.04 (s, 3 H) 2.05 (s, 3 H) 2.28 (s, 3 H) 2.90 (sept, J=6.68 Hz, 1 H) 3.71-3.90 (m, 3 H) 3.86 (s, 3 H) 4.05-4.15 (m, 1 H) 4.19-4.28 (m, 1 H) 4.77-4.85 (m, 1 H) 5.11-5.23 (m, 1 H) 5.26-5.37 (m, 2 H) 6.54 (d, J=8.24 Hz, 1 H) 6.81 (s, 1 H) 6.96 (s, 1 H) 7.17 (dd, J=8.24, 2.64 Hz, 1 H) 7.32 (d, J=2.64 Hz, 1 H).

MS ESI/APCI Dual posi: 685[M+Na]⁺, 687[M+2+Na]⁺.

REFERENCE EXAMPLE 2

Production of Intermediate (A)

To a solution of 3-isopropylphenol (160 g, 1.18 mol) in acetic acid (1.6 L), a solution of bromine (469 g, 2.94 mol) in acetic acid (320 mL) was added dropwise over 32 minutes, under ice cooling such that the internal temperature did not exceed 19° C., and the mixture was stirred at room temperature for 1 hour. After addition of toluene (1.6 L), the mixture was cooled on ice. A 10% aqueous solution of sodium sulfite (1.0 L) was added dropwise such that the internal temperature did not exceed 20° C., to separate the organic layer. The organic layer was washed twice with a 10% aqueous solution of sodium sulfite (1.0 L) and a 10% aqueous solution of sodium chloride (1.0 L), and then dried over anhydrous magnesium sulfate. After filtering off the desiccant, the solvent was distilled off under reduced pressure to give 2,4-dibromo-5-isopropylphenol (342 g, 99%) as a light yellow oil.

$^1$H NMR (300 MHz, CHLOROFORM-d) δ ppm 1.21 (d, J=6.84 Hz, 6 H) 3.25 (sept, J=6.84 Hz, 1 H) 5.40 (s, 1 H) 6.96 (s, 1 H) 7.61 (s, 1 H).

To a solution of 2,4-dibromo-5-isopropylphenol (512 g, 1.74 mol) in chloroform (1.74 L), N,N-diisopropylethylamine (364 mL, 2.09 mol) was added, and cooled on ice. Chloromethyl methyl ether (159 mL, 2.09 mol) was added dropwise over 60 minutes, and the mixture was stirred at room temperature for 1 hour. The reaction mixture was cooled on ice, and a 1M aqueous solution of sodium hydroxide (1.5 L) was added dropwise to separate the organic layer. The organic layer was washed with a 1M aqueous solution of sodium hydroxide (1.5 L) and water (1.5 L), and then dried over anhydrous magnesium sulfate. After filtering off the desiccant, the solvent was distilled off under reduced pressure. The resulting residue was purified by distillation under reduced pressure (0.93 to 1.5 hpa, 122° C. to 137° C.) to give 1,5-dibromo-2-isopropyl-4-(methoxymethoxy)benzene (548 g, 96%) as a light yellow oil.

$^1$H NMR (300 MHz, CHLOROFORM-d) δ ppm 1.22 (d, J=6.84 Hz, 6 H) 3.28 (sept, J=6.84 Hz, 1 H) 3.52 (s, 3 H) 5.23 (s, 2 H) 7.06 (s, 1 H) 7.69 (s, 1 H).

MS ESI/APCI Dual posi: 339[M+H]$^+$, 341[M+2+H]$^+$.

To a solution of 1,5-dibromo-2-isopropyl-4-(methoxymethoxy)benzene (200 g, 0.592 mol) in tetrahydrofuran (2.84 L), a solution of 2.69M n-butyllithium in hexane (231 mL, 0.621 mol) was then added dropwise over 20 minutes at −80° C. to −76° C. under an argon atmosphere, followed by stirring the mixture at the same temperature for 35 minutes. Then, a solution of 2,3,4,6-tetra-O-trimethylsilyl-D-glucono-1,5-lactone (290 g, 0.621 mol) in tetrahydrofuran (800 mL) was added dropwise over 55 minutes, and the mixture was stirred at the same temperature for 50 minutes. Further, trimethylchlorosilane (75.7 mL, 0.621 mol) was added dropwise over 15 minutes, and the mixture was stirred at the same temperature for 2 hours. Then, a solution of 2.69M n-butyllithium in hexane (319 mL, 0.858 mol) was added dropwise over 29 minutes, and the mixture was stirred at the same temperature for 40 minutes. Finally, a solution of 4-bromo-2-methylbenzaldehyde (130 g, 0.651 mol) in tetrahydrofuran (800 mL) was added dropwise over 54 minutes, and the mixture was stirred at the same temperature for 30 minutes. Water (2.85 L) was added to the reaction mixture, and the resulting mixture was warmed to room temperature. Toluene (2.0 L) was added to separate the organic layer, and the solvent was distilled off under reduced pressure.

The resulting residue (546 g) was dissolved in methanol (3.0 L), and methanesulfonic acid (3.84 mL, 0.0592 mol) was added, followed by heating under reflux for 1.5 hours. The reaction mixture was cooled to room temperature, and then neutralized with triethylamine (25 mL, 0.179 mol), and the reaction mixture was concentrated. The concentrate was dissolved in toluene (1.0 L), and washed with water (0.5 L, 1.0 L). To the organic layer, a 1M aqueous solution of sodium hydroxide (0.6 L) and toluene (1.0 L) were added for extraction, to separate the aqueous layer. The aqueous layer was washed with toluene (0.5 L). To the aqueous layer, 10% hydrochloric acid (0.7 L) was added, and the mixture was extracted with toluene (1.0 L). The organic layer was washed with a 10% aqueous solution of sodium chloride (1.0 L) and water (0.5 L), and the solvent was distilled off under reduced pressure.

The resulting residue (314 g) was dissolved in pyridine (1.0 L), and acetic anhydride (0.8 L, 8.51 mol) was added, followed by stirring the mixture for 18 hours at room temperature. The reaction mixture was cooled on ice, and ice (1.5 L) and toluene (1.0 L) were added, and the mixture was stirred for 3 hours. The organic layer was separated, and then the aqueous layer was extracted with toluene (1.0 L). The organic layer combined was washed with 2M hydrochloric acid (1.5 L) twice, and further with a 5% aqueous solution of sodium hydrogen carbonate (1.0 L), and a 10% aqueous solution of sodium chloride (1.0 L), whereafter the solvent was distilled off under reduced pressure.

The resulting residue (350 g) was dissolved in acetonitrile (3.4 L), and water (9.1 mL, 0.506 mol) and Et$_3$SiH (328 mL, 2.05 mol) were added to the solution. Under ice cooling of the mixture, TMSOTf (403 mL, 2.23 mol) was added dropwise over 85 minutes. The mixture was stirred at the same temperature for 2 hours, and then a 3% aqueous solution of sodium hydrogen carbonate (1.92 L) was added dropwise over 40 minutes. The reaction mixture was diluted with toluene (1.0 L) and stirred for 15 minutes, whereafter the organic layer was separated. The aqueous layer was extracted with toluene (1.5 L). The organic layer combined was washed with a saturated aqueous solution of sodium hydrogen carbonate (1.50 L), and the solvent was distilled off under reduced pressure to give colorless liquid compound (A7) (392 g).

[Chemical Formula 14]

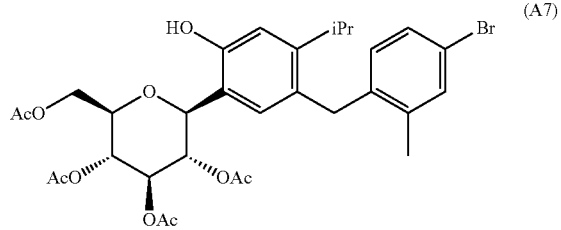

$^1$H NMR (300 MHz, CHLOROFORM-d) δ ppm 1.09-1.19 (m, 6 H) 1.69 (s, 3 H) 1.99 (s, 3 H) 2.05 (s, 3 H) 2.12 (s, 3 H) 2.25 (s, 3 H) 2.80-2.97 (m, 1 H) 3.66-3.96 (m, 3 H) 4.08-4.35 (m, 2 H) 4.42-4.57 (m, 1 H) 5.19-5.37 (m, 3 H) 6.52 (s, 1 H) 6.57 (d, J=8.1 Hz, 1 H) 6.87 (s, 1 H) 7.12-7.20 (m, 1 H) 7.30-7.33 (m, 1 H).

A solution of methyl iodide (33 mL, 0.53 mol) in N,N-dimethylformamide (50 mL) was added dropwise to a suspension of compound (A7) (392 g, 0.506 mol) and potassium carbonate (73.4 g, 0.531 mol) in N,N-dimethylformamide (0.95 L). The reaction mixture was stirred for 1 hour, and then potassium carbonate (70.0 g, 0.506 mol) and methyl iodide (31.5 mL, 0.506 mol) were added, followed by stirring the mixture for 1 hour. Potassium carbonate (70.0 g, 0.506 mol) and methyl iodide (31.5 mL, 0.506 mol) were added again, and the mixture was stirred for 1 hour. Methyl iodide (15.8 mL, 0.254 mol) was added, and the mixture was stirred overnight at room temperature. The reaction mixture was stirred at 50° C. for 2 hours and then diluted with toluene (1.25 L), whereupon water (1.0 L) was added. Two layers were separated, and the organic layer was washed with water (1.0 L) twice, and with a 10% aqueous solution of sodium chloride (1.0 L), and then concentrated under reduced pressure. Isopropyl alcohol (350 mL) was added to the resulting residue, and the mixture was dissolved with heating at 40° C., whereafter the solution was stirred at room temperature. The resulting precipitate was filtered off and dried to give intermediate (A) (155 g, 46%) as a colorless powder.

REFERENCE EXAMPLE 3

Production of Intermediate (B)

[Chemical Formula 15]

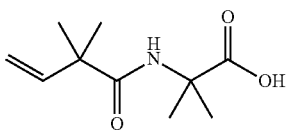

(B)

(1) Step 1 Compound (B1)

[Chemical Formula 16]

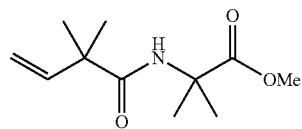

(B1)

To a solution of 2,2-dimethyl-3-butenoic acid (J. Org. Chem., Vol. 65, p. 8402, 2000) (5.42 g, 47.5 mmol) in chloroform (250 mL), oxalyl chloride (4.43 mL, 49.9 mmol) and N,N-dimethylformamide (3 drops) were added under a nitrogen atmosphere, and the mixture was stirred at room temperature for 1.5 hours. Then, the reaction mixture was cooled on ice, and triethylamine (19.9 mL, 143 mmol) and α-aminoisobutyric acid methyl ester hydrochloride (10.9 g, 71.2 mmol) were added, followed by stirring the mixture at room temperature for 1 hour. Water was added to the reaction mixture, and the resulting mixture was extracted with chloroform. Then, the organic layer was washed with 3M hydrochloric acid, a saturated aqueous solution of sodium hydrogen carbonate and brine, and dried over anhydrous magnesium sulfate. After filtering off the desiccant, the solvent was distilled off under reduced pressure. The resulting residue was purified by silica gel column chromatography (hexane÷hexane:ethyl acetate=4:1) to give colorless powdery compound (B1) (9.38 g, 93%).

$^1$H NMR (300 MHz, CHLOROFORM-d) δ ppm 1.27 (s, 6 H) 1.51 (s, 6 H) 3.73 (s, 3 H) 5.17-5.32 (m, 2 H) 6.02 (dd, J=17.56, 10.57 Hz, 1 H) 6.25 (br. s., 1 H).

MS ESI/APCI Dual posi: 214[M+H]$^+$.

(2) Step 2 Intermediate (B)

[Chemical Formula 17]

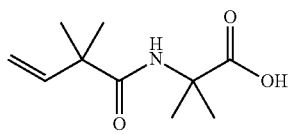

(B)

A 4M aqueous solution of sodium hydroxide (16.5 mL, 66.0 mmol) was added to a solution of compound (B1) (9.38 g. 43.9 mmol) in methanol (20 mL), and the mixture was stirred at room temperature for 1 hour. Then, the reaction mixture was concentrated. The resulting residue was dissolved in water, and the solution was neutralized with the addition of 3M hydrochloric acid. This mixture was extracted with ethyl acetate, and the organic layer combined was washed with brine, and dried over anhydrous magnesium sulfate. After filtering off the desiccant, the solvent was distilled off under reduced pressure to give colorless powdery intermediate (B) (8.19 g, 94%).

$^1$H NMR (300 MHz, CHLOROFORM-d) δ ppm 1.29 (s, 6 H) 1.54 (s, 6 H) 5.16-5.36 (m, 2H) 6.01 (dd, J=17.49, 10.65 Hz, 1 H) 6.14 (s, 1 H).

MS ESI/APCI Dual posi: 200[M+H]$^+$, 222[M+Na]$^+$.

MS ESI/APCI Dual nega: 198[M−H]$^-$.

REFERENCE EXAMPLE 4

Production of Intermediate (C)

[Chemical Formula 18]

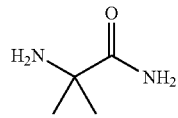

(C)

To a solution of 2-((benzyloxycarbonyl)amino)-2-methylpropionic acid (10.0 g, 42.2 mmol) in acetonitrile (200 mL), di-tert-butyl dicarbonate (12 mL, 55.3 mmol), ammonium carbonate (4.0 mL, 50.6 mmol) and pyridine (2.6 mL, 32.1 mmol) were added. The reaction mixture was stirred at room temperature for 3 hours, and concentrated. The resulting solids were washed with water and dried to obtain a colorless powder (9.8 g). This powder (5.0 g) was dissolved in methanol (100 mL), and 5% Pd—C (0.5 g) was added. This mixture was stirred for 3.5 hours under a hydrogen atmosphere. The reaction mixture was filtered through Celite (registered trademark), and then the solvent was distilled off under reduced pressure to give intermediate (C) (1.7 g).

$^1$H NMR (300 MHz, DMSO-d$_6$) δ ppm 1.15 (s, 6 H) 1.64-1.95 (brs, 2 H) 6.68-6.93 (brs, 1 H) 7.11-7.40 (brs, 1 H).

EXAMPLE 1

Synthesis of Compound (I)

(1) Step 1 Compound (1-1)

[Chemical Formula 19]

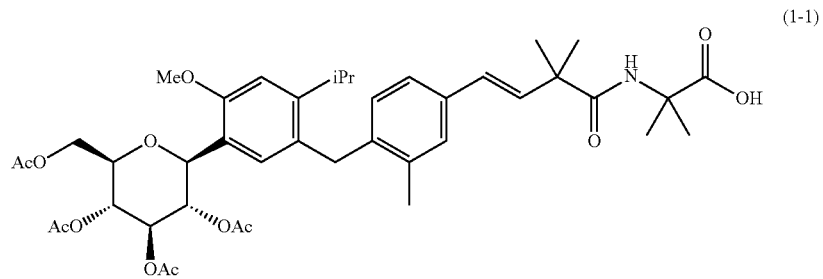

Under an argon atmosphere, a suspension of intermediate (A) (2.0 g, 3.0 mmol), intermediate (B) (1.08 g, 5.4 mmol), palladium(II) acetate (136 mg, 0.60 mmol), tri-o-tolylphosphine (370 mg, 1.20 mmol), and triethylamine (1.26 mL, 9.00 mmol) in acetonitrile (10 mL) was stirred at 120° C. for 20 minutes under microwave irradiation. The reaction mixture was filtered through Celite (registered trademark), and washed with ethyl acetate. The filtrate was concentrated under reduced pressure, and the resulting residue was purified by silica gel column chromatography (hexane:ethyl acetate=1:1→ethyl acetate) to give light yellow powdery compound (1-1) (2.03 g, 87%).

$^1$H NMR (300 MHz, CHLOROFORM-d) δ ppm 1.17, 1.14 (each d, J=6.99 Hz, 3 H) 1.38 (s, 6 H) 1.55 (s, 6 H) 1.76 (s, 3 H) 1.98 (s, 3 H) 2.04 (s, 6 H) 2.30 (s, 3 H) 2.94-3.03 (m, 1 H) 3.76-3.83 (m, 1 H) 3.84-3.95 (m, 4 H) 4.06-4.15 (m, 1 H) 4.16-4.25 (m, 1 H) 4.74-4.89 (m, 1 H) 5.12-5.20 (m, 1 H) 5.23-5.35 (m, 2 H) 6.29 (s, 1 H) 6.31 (d, J=16.32 Hz, 1 H) 6.52 (d, J=16.32 Hz, 1 H) 6.67 (d, J=8.08 Hz, 1 H) 6.81 (s, 1 H) 6.94 (s, 1 H) 7.06-7.14 (m, 1 H) 7.24 (s, 1 H).

MS ESI/APCI Dual posi: 782[M+H]$^+$, 804[M+Na]$^+$.
MS ESI/APCI Dual nega: 780[M−H]$^-$.

(2) Step 2 Compound (1-2)

To a solution of intermediate (1-1) (100 mg, 0.128 mmol), HOBt.H$_2$O (29.4 mg, 0.192 mmol), and a 28% aqueous solution of ammonia (23.3 mg, 0.384 mmol) in N,N-dimethylformamide (1.2 mL), EDC-HCl (36.8 mg, 0.192 mmol) was added, and the mixture was stirred for 15 hours at room temperature. The reaction mixture was poured into water (50 mL), and the resulting mixture was extracted with ethyl acetate (50 mL). The organic layer was washed with brine (20 mL), and dried over anhydrous magnesium sulfate. After filtering off the desiccant, the solvent was distilled off under reduced pressure. The resulting residue was purified by silica gel column chromatography (chloroform→chloroform:methanol=9:1) to give colorless amorphous compound (1-2) (58 mg, 58%).

$^1$H NMR (300 MHz, CHLOROFORM-d) δppm 1.10-1.17 (m, 6 H) 1.38 (s, 6 H) 1.52 (s, 6 H) 1.77 (s, 3 H) 1.99 (s, 3 H) 2.04 (s, 3 H) 2.04 (s, 3 H) 2.32 (s, 3 H) 2.95 (sept, J=6.9 Hz, 1H) 3.76-3.95 (m, 6 H) 4.08-4.14 (m, 1 H) 4.18-4.26 (m, 1 H) 4.79-4.85 (m, 1 H) 5.13-5.22 (m, 1 H) 5.27-5.36 (m, 2 H) 6.29 (d, J=16.3 Hz, 1 H) 6.51 (d, J=16.3 Hz, 1 H) 6.66 (d, J=7.9 Hz, 1 H) 6.81 (s, 1 H) 6.98 (s, 1 H) 7.09 (dd, J=7.9, 1.4 Hz, 1 H) 7.23 (d, J=1.4 Hz, 1H).

[Chemical Formula 20]

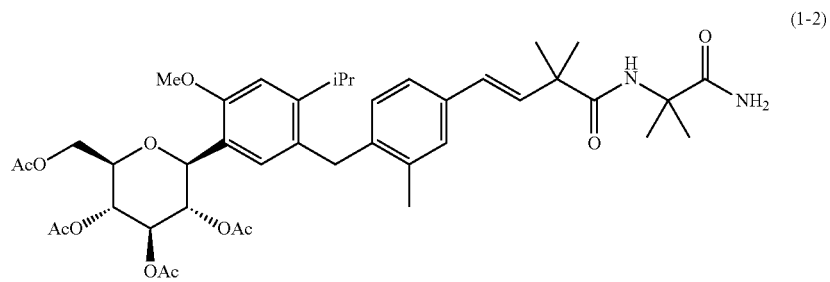

(3) Step 3 Compound (I)

[Chemical Formula 21]

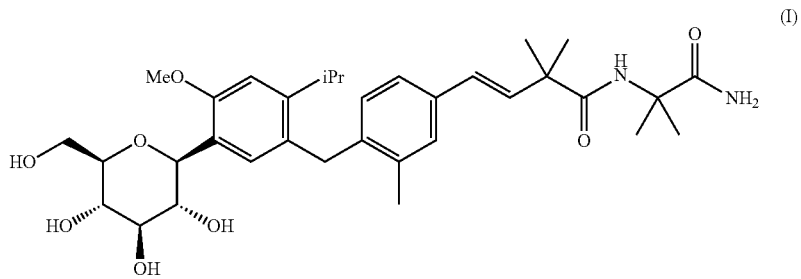

To a solution of compound (1-2) (52 mg, 0.066 mmol) in methanol (0.5 mL), sodium methoxide (4.88M/MeOH, 15 µL) was added, and the reaction mixture was stirred at room temperature for 0.5 hour. A small amount of dry ice was added to neutralize the reaction mixture. Then, the solvent was distilled off under reduced pressure.

The resulting residue was purified by NH type silica gel chromatography (chloroform:methanol=85:15) to give colorless amorphous compound (I) (40 mg, 98%).

$^1$H NMR (600 MHz, METHANOL-$d_4$) δppm 1.13-1.16 (m, 6 H) 1.35 (s, 6 H) 1.50 (s, 6 H) 2.32 (s, 3 H) 2.95-3.03 (m, 1 H) 3.32-3.38 (m, 2 H) 3.44-3.48 (m, 1 H) 3.49-3.54 (m, 1H) 3.59-3.63 (m, 1 H) 3.80-3.86 (m, 4 H) 3.91 (s, 2 H) 4.61 (d, J=9.6 Hz, 1 H) 6.37 (d, J=16.0 Hz, 1 H) 6.50 (d, J=16.0 Hz, 1 H) 6.74 (d, J=7.8 Hz, 1 H) 6.92 (s, 1 H) 7.07 (s, 1 H) 7.11 (d, J=7.8 Hz, 1 H) 7.25 (s, 1 H) 7.29 (s, 1 H).

MS ESI/APCI Dual posi: 613[M+H]$^+$, 635[M+Na]$^+$.
MS ESI/APCI Dual nega: 611[M−H]$^−$, 647[M+Cl]$^−$.

EXAMPLE 2

Synthesis of Compound (I)

Step 1 Compound (2-1)

[Chemical Formula 22]

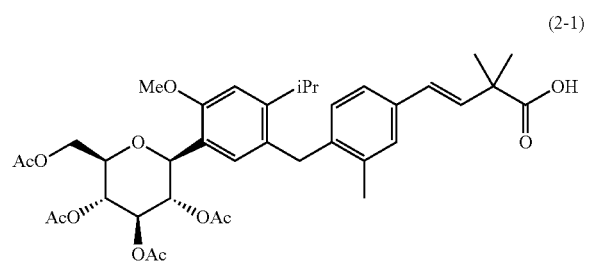

Under an argon atmosphere, a suspension of intermediate (A) (100 g, 0.151 mol), 2,2-dimethyl-3-butenoic acid (25.8 g, 0.226 mol), palladium(II) acetate (3.39 g, 15.1 mmol), tri-o-tolylphosphine (9.16 g, 30 1 mmol), and triethylamine (63 mL) in acetonitrile (300 mL) was heated under reflux for 3 hours. The reaction mixture was cooled to room temperature, then diluted with chloroform (300 mL) and methanol (100 mL), and filtered through Celite (registered trademark). The filtrate was concentrated under reduced pressure, and the resulting residue was dissolved in ethyl acetate (1.32 L). The solution was washed with 1M hydrochloric acid (0.96 L) and a 10% aqueous solution of sodium chloride (1.2 L), and dried over anhydrous magnesium sulfate. The desiccant was filtered off, whereafter isopropylamine (13.0 mL, 0.151 mol) was added to the filtrate, and the mixture was stirred at room temperature to 0° C. for 1 hour. The resulting precipitate was filtered to give an isopropylamine salt of intermediate (2-1). This salt was dissolved in ethyl acetate (1.2 L) and 1M hydrochloric acid (500 mL), and the solution was stirred for 30 minutes to separate the organic layer. The organic layer was washed with a 10% aqueous solution of sodium chloride (500 mL), and dried over anhydrous magnesium sulfate. After filtering off the desiccant, the solvent was distilled off under reduced pressure to obtain colorless amorphous compound (2-1) (113 g).

$^1$H NMR (600 MHz, CHLOROFORM-d) δ ppm 1.12 (d, J=6.9 Hz, 3 H) 1.13 (d, J=6.9 Hz, 3H) 1.43 (s, 6 H) 1.75 (s, 3 H) 1.99 (s, 3 H) 2.02-2.07 (m, J=1.8 Hz, 6 H) 2.29 (s, 3 H) 2.85-3.02 (m, 1 H) 3.77-3.81 (m, 1 H) 3.81-3.91 (m, 5 H) 4.08-4.13 (m, 1 H) 4.21 (dd, J=12.2, 4.4 Hz, 1 H) 4.79 (br. d, J=8.3 Hz, 1 H) 5.17 (t, J=9.6 Hz, 1 H) 5.27-5.36 (m, 2 H) 6.35 (d, J=16.3 Hz, 1 H) 6.43 (d, J=16.3 Hz, 1 H) 6.64 (d, J=8.3 Hz, 1 H) 6.80 (s, 1 H) 6.95 (s, 1 H) 7.06 (dd, J=8.0, 1.6 Hz, 1 H) 7.21 (br. s, 1 H).

(2) Step 2 Compound (1-2)

[Chemical Formula 23]

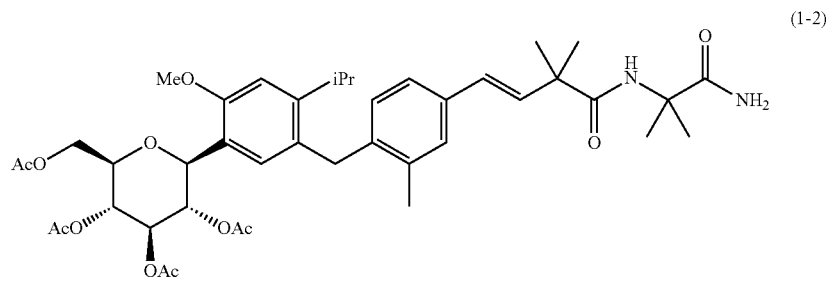

(1-2)

To a solution of compound (2-1) (113 g, 0.151 mol), intermediate (C) (23.2 g, 0.227 mol) and HOBt.H₂O (34.7 g, 0.227 mol) in N,N-dimethylformamide (0.79 L), EDC-HCl (43.4 g, 0.226 mol) was added, and the mixture was stirred at room temperature for 24 hours. Toluene (1.0 L) and a 10% aqueous solution of sodium chloride (2.0 L) were added to the reaction mixture to separate the organic layer. The aqueous layer was extracted with toluene (1.0 L), and the organic layer combined was washed with a 5% aqueous solution of sodium chloride (1.0 L), and dried over anhydrous magnesium sulfate. After filtering off the desiccant, the solvent was distilled off under reduced pressure. The resulting residue was purified by silica gel column chromatography (chloroform:methanol=80:20) to give light yellow amorphous compound (1-2) (108 g, 92%).

(3) Step 3 Synthesis of Compound (I)

[Chemical Formula 24]

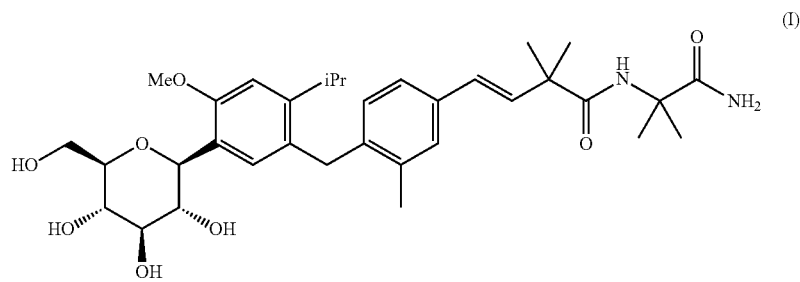

(I)

Compound (1-2) (107 g, 0.137 mol) was dissolved in methanol (0.5 L) and, after the solution was cooled on ice, triethylamine (0.1 L) and water (0.1 L) were added. The mixture was stirred at room temperature for 20 hours. The reaction mixture was concentrated, and azeotropically distilled with methanol. The resulting residue was dissolved in methanol (0.3 L), water (0.4 L) was added to the solution, and the mixture was stirred. The resulting residue was filtered, washed with water, and dried to give colorless powdery compound (I) (70 g, 83%).

The compound (I) had peaks at 2θ=11.50 degrees, 16.10 degrees and 20.84 degrees in X-ray powder diffraction (Cu—Kα). Its melting point was 135° C.

TEST EXAMPLE 1

(1) Creation of CHO-K1 Cells Stably Expressing Human SGLT1

A plasmid vector expressing human SGLT1 protein was transfected into CHO-K1 cells using Lipofectamine 2000 (Invitrogen). The cells were cultured in the presence of 500 μg/mL geneticin to select resistant strains, followed by screening in the system shown below using sugar uptake capacity as an indicator to obtain SGLT1-expressing cells.

(2) Creation of CHO-K1 Cells Stably Expressing Human SGLT2

A plasmid vector expressing human SGLT2 protein was transfected into CHO-K1 cells using Lipofectamine LTX (Invitrogen). The cells were cultured in the presence of 1000 μg/mL geneticin to select resistant strains, followed by screening in the system shown below using sugar uptake capacity as an indicator to obtain SGLT2-expressing cells.

(3) Inhibition Test of Sodium-Dependent Glucose Uptake in Stable Expression Cells The stably expressing cells prepared above were used in the following test.

Pretreatment buffer (140 mM choline chloride, 2 mM KCl, 1 mM CaCl₂, 1 mM MgCl₂, 10 mM HEPES/5 mM Tris, pH 7.4) was added to the stably expressing cells, followed by incubation for 20 minutes. The pretreatment buffer was removed and replaced by uptake buffer containing a test compound (1 mM methyl α-D-glucopyranoside (containing [$^{14}$C]methyl α-D-glucopyranoside), 145 mM NaCl, 2 mM KCl, 1 mM CaCl$_2$, 1 mM MgCl$_2$, 10 mM HEPES/5 mM Tris, pH 7.4). Uptake reaction was performed at 37° C. for 30 minutes (SGLT1) or 60 minutes (SGLT2). After the reaction, the cells were washed twice with washing buffer (10 mM methyl α-D-glucopyranoside, 140 mM choline chloride, 2 mM KCl, 1 mM CaCl$_2$, 1 mM MgCl$_2$, 10 mM HEPES/5 mM Tris, pH 7.4), and then dissolved in a 0.25 M NaOH solution. A liquid scintillator (Perkin Elmer) was added and mixed well, followed by measurement of radioactivity using a β-ray analyzer. For the control group, uptake buffer containing no test compound was prepared. Moreover, another uptake buffer containing choline chloride instead of NaCl was also prepared for basal uptake.

For determination of IC$_{50}$ values, test compounds prepared at 6 appropriate concentrations were used and their concentrations required for 50% inhibition of the amount of sugar uptake (IC$_{50}$ values) were calculated relative to the amount of sugar uptake in the control group (100%). The test results on compound (I) are shown in Table 1.

TABLE 1

| Compound | IC$_{50}$ for hSGLT1 (nM) | IC$_{50}$ for hSGLT2 (nM) |
|---|---|---|
| (I) | 65 | 554 |

TEST EXAMPLE 2

(1) Changes in Renal Concentrations of Compounds 4, 10, 11 and 33 Disclosed in WO2007/136116 Until One Week After Oral Administration SD/IGS rats at 7 weeks of age (male, non-fasting, Charles River Laboratories Japan Inc.) were orally administered with compound 4, 10 or 33 (1 mg/kg each) or compound 11 (0.3 mg/kg) prepared in a 0.5% aqueous solution of CMC. At 24, 72 and 168 hours after drug administration, the rats were exsanguinated via the postcaval vein under ether anesthesia, and their kidneys were excised after they were confirmed to be euthanized. After the tissue surface was washed with physiological saline, each tissue was measured for its weight and homogenized in 4 volumes of purified water under ice cooling. To each homogenate, an acetonitrile/methanol solution containing an internal standard substance was added to remove proteins, and the supernatant was then subjected to LC-MS/MS (Applied Biosystems API3000). Drug-derived ions generated by electrospray ionization in positive ion mode were detected by selective reaction monitoring. The peak area of the resulting extracted ion chromatogram was analyzed by the internal standard method to calculate the drug concentration in the homogenate.

As the internal standard material for compounds 10 and 33, (1S)-1,5-anhydro-1-[5-(4-ethoxybenzyl)-2-methoxy-4-methylphenyl]-1-thio-D-glucitol,ethyl-D$_5$ was used. As the internal standard materials for compounds 4 and 11, compound 11 and deuterium-labeled compound 11 (trishydroxymethyl-D$_6$; —C(CD$_2$OH)$_3$), respectively, were used.

The experimental results obtained are shown in Table 2.

(2) Renal Concentrations of the Compound (I) of the Present Invention After Repeated Oral Administration for 3 Days SD/IGS rats at 7 weeks of age (male, non-fasting, Charles River Laboratories Japan Inc.) were orally administered once a day for 3 consecutive days with the compound (I) (3 mg/kg) prepared in a 0.5% aqueous solution of CMC. At 48 hours after the final drug administration, the rats were exsanguinated via the postcaval vein under isoflurane anesthesia, and their kidneys were excised after they were confirmed to be euthanized. After the tissue surface was washed with physiological saline, each tissue was measured for its weight and homogenized in 4 volumes of purified water under ice cooling. The drug concentration in each homogenate was determined in the same manner as shown in Test Example 2(1) by LC-MS/MS using compound 11 as an internal standard substance.

The experimental results are shown in Table 3.

Test Example 3 Confirmation study of hypoglycemic effect in streptozotocin diabetic model rats (1) Preparation of Diabetic Model Rats SD/IGS rats at 7 weeks of age (male, Charles River Laboratories Japan Inc.) were fasted for about 16 hours and then injected with 50 mg/kg streptozotocin (STZ) via the caudal vein under ether anesthesia to prepare diabetic model rats. Similarly, another group of SD/IGS rats at 7 weeks of age was injected with 1.25 mmol/L citric acid in physiological saline (1 mL/kg) via the caudal vein under ether anesthesia to prepare normal control rats. At one week after injection of STZ or 1.25 mmol/L citric acid in physiological saline, the rats (8 weeks old) were provided for an oral glucose tolerance test.

(2) Oral Glucose Tolerance Test

After the diabetic model rats were fasted for about 16 hours, drug groups were each orally administered with a drug (1 mg/kg) dissolved in a 0.5% aqueous solution of carboxymethylcellulose sodium (CMC), while the control group was orally administered with a 0.5% aqueous solution of CMC alone. At 5 minutes after drug administration, a glucose solution (2 g/kg) was orally administered to each rat, and the blood was collected at a total of 5 time points: before drug administration (0 time), and at 0.25, 0.5, 1 and 2 hours after the oral administration.

Blood was collected from the caudal veins of the rats under ether anesthesia with the use of a heparin-coated blood collecting tube and centrifuged, whereafter blood plasma was separated. Plasma glucose concentrations were quantified by measurement with a Glucose CII-Test Wako (Wako Pure Chemical Industries, Ltd., Japan). To determine the intensity of hypoglycemic effect, the blood glucose level before drug administration was subtracted from each blood glucose level measured until one hour after oral administration in each drug group, and the resulting values were analyzed by the trapezoidal method to calculate an increment in the area under the curve for glucose (ΔAUC), which was expressed as a decrease relative to ΔAUC of the control group.

The results obtained are shown in Table 2 and Table 3.

TABLE 2

Glucose tolerance test results and renal concentrations of prior art compounds

| compound No. in WO2007/ 136116 | STZ rats OGTT$ % inhibition ΔAUC$_{0-1h}$ (mg/dl) @ 1 mg/kg/po | Concentration of compounds in kidney after single oral administration at a dose of 1 mg/kg to male Sprague-Dawley rats. | | |
|---|---|---|---|---|
| | | After 1 day (ng/g) | After 3 days (ng/g) | After 7 days (ng/g) |
| compound 4 | 51 | 68.4 ± 7.49 | 85.5 ± 23.1 | 76.3 ± 15.5 |
| compound 10 | 69 | 167 ± 36.3 | 124 ± 12.2 | 53.8 ± 7.6 |
| compound 11 | 68 | 63.5 ± 20.1* | 67.3 ± 3.15* | 48.7 ± 18.3* |
| compound 33 | 81[#] | 29.8 ± 6.79 | 25.5 ± 8.68 | 16.2 ± 3.11 |

*The value represents mean ± S.D. when compound 11 was orally administered at 0.3 mg/kg.
$Suppression of glucose AUC$_{0-1h}$ in streptozotocin (STZ)-induced diabetic rats versus vehicle control, following an oral dose at 1 mg/kg.
[#]OGTT using Sprague-Dawley rats.

The structures of compounds 4, 10, 11 and 33 disclosed in International Patent Publication WO2007/136116 pamphlet are shown below.

[Chemical Formula 25]

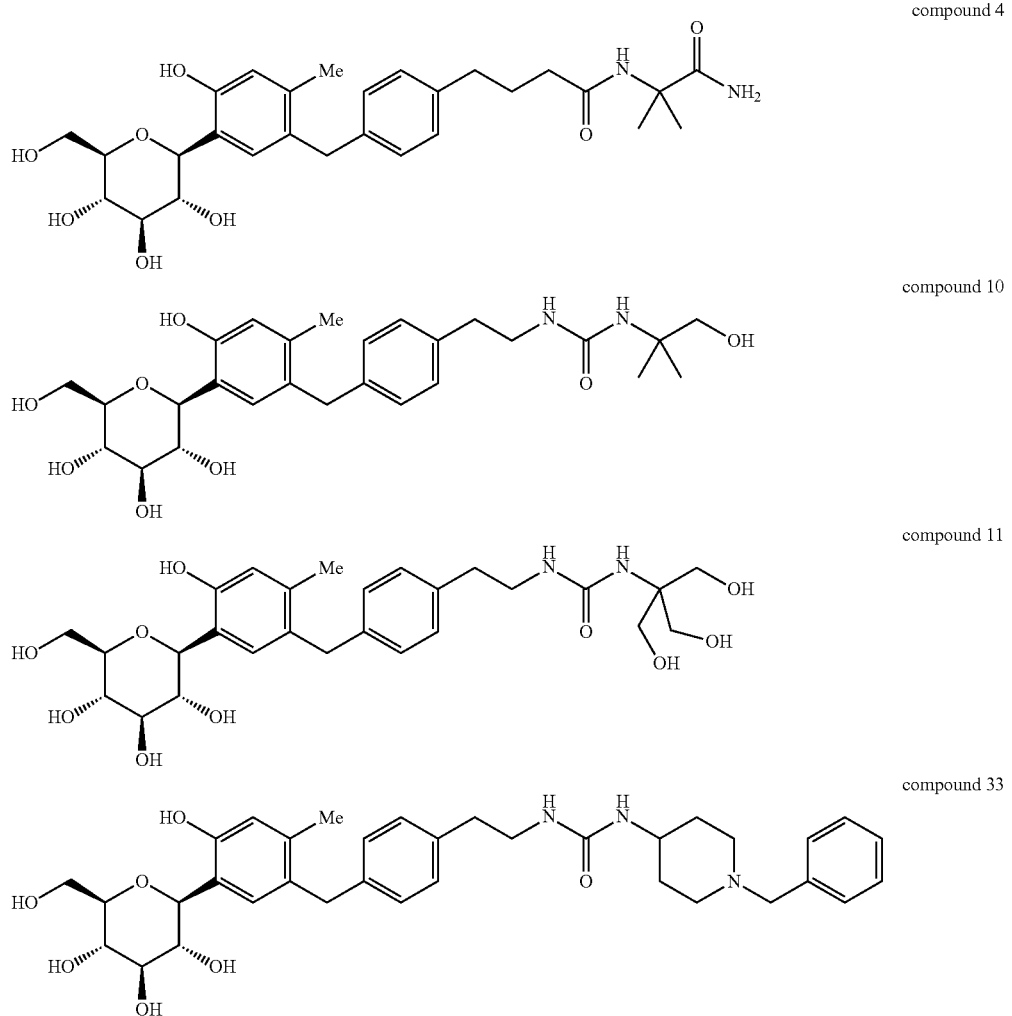

compound 4 compound 10 compound 11 compound 33

TABLE 3

Glucose tolerance test results and renal concentrations of the compound of the present invention

| Compound No. | STZ rats OGTT* % inhibition $\Delta AUC_{0-1h}$ (mg/dl) @ 3 mg/kg/po | Concentration of compounds in kidney after 3 days continuous oral administration at a dose of 3 mg/kg to male Sprague-Dawley rats. After 2 days (ng/g) |
|---|---|---|
| (I) | 54 | ND[#] |

*Suppression of glucose $AUC_{0-1h}$ in STZ-induced diabetic rats versus vehicle control, following an oral dose at 1 mg/kg.
[#]ND (not determined) means limit of detection (5 ng/g).

The compounds disclosed in WO2007/136116 exhibited potent hypoglycemic action in the glucose tolerance test after oral administration of 1 mg/kg. Following the oral administration of 1 mg/kg, however, the elimination rates of the compounds from within the kidney were so slow that the compounds tended not to be excreted, but to remain in the kidney, even after 7 days (Table 2).

On the other hand, the compound (I) of the present invention had potent hypoglycemic action, like the above-mentioned prior art compounds. Moreover, this compound exhibited a characteristic feature in that even when it was administered in a dose of 3 mg/kg for 3 consecutive days, it unexpectedly did not remain in the kidney at subsequent day 2 (Table 3).

A possible cause of this difference is that the compound of the present invention has been rapidly excreted, without remaining in the kidney, when absorbed in the body.

Thus, the compound of the present invention does not remain in the body and is less likely to cause side effects and toxicity due to continuous administration, and hence is excellent in practical applicability as a pharmaceutical preparation.

Industrial Applicability

The present invention enables the provision of a drug for improving postprandial hyperglycemia which has strong SGLT1 inhibitory activity and does not remain in the body. The present invention also contributes to an improvement in human health and facilitates the wholesome development of the pharmaceutical industry through contribution to the treatment and prevention of postprandial hyperglycemia-induced diseases against which inhibition of SGLT1 activity is effective.

The invention claimed is:

1. A 4-isopropyl-6-methoxyphenyl glucitol compound represented by the following formula (I), or a pharmaceutically acceptable salt thereof:

[Chemical Formula 1]

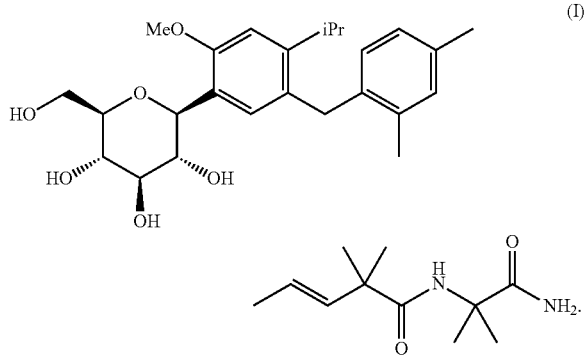

2. A pharmaceutical composition which comprises the 4-isopropyl-6-methoxyphenyl glucitol compound according to claim 1 or the pharmaceutically acceptable salt thereof as an active ingredient and a pharmaceutically acceptable carrier(s).

3. A method of inhibiting sodium-dependent glucose transporter 1 (SGLT1) activity which comprises administering the 4-isopropyl-6-methoxyphenyl glucitol compound according to claim 1 or the pharmaceutically acceptable salt thereof to a patient in need thereof.

4. A method of improving postprandial hyperglycemia which comprises administering the 4-isopropyl-6-methoxyphenyl glucitol compound according to claim 1 or the pharmaceutically acceptable salt thereof to a patient in need thereof.

5. A method of treating diabetes which comprises administering the 4-isopropyl-6-methoxyphenyl glucitol compound according to claim 1 or the pharmaceutically acceptable salt thereof to a patient in need thereof.

* * * * *